United States Patent
Uppaluri et al.

(10) Patent No.: US 7,263,214 B2
(45) Date of Patent: *Aug. 28, 2007

(54) COMPUTER AIDED DIAGNOSIS FROM MULTIPLE ENERGY IMAGES

(75) Inventors: Renuka Uppaluri, Pewaukee, WI (US); Amber Elaine Rader, New Berlin, WI (US); Gopal B. Avinash, New Berlin, WI (US); Carson Hale Thomas, Brookfield, WI (US); John Michael Sabol, Sussex, WI (US); Kadri Nizar Jabri, Waukesha, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 643 days.

This patent is subject to a terminal disclaimer.

(21) Appl. No.: 10/063,819

(22) Filed: May 15, 2002

(65) Prior Publication Data

US 2003/0215119 A1 Nov. 20, 2003

(51) Int. Cl.
*G06K 9/00* (2006.01)
(52) U.S. Cl. .................. 382/128; 382/190; 382/130
(58) Field of Classification Search ........ 382/128–134, 382/190
See application file for complete search history.

(56) References Cited

U.S. PATENT DOCUMENTS

| 4,792,900 A | * | 12/1988 | Sones et al. | 600/407 |
|---|---|---|---|---|
| 4,837,686 A | * | 6/1989 | Sones et al. | 378/18 |
| 5,115,394 A | | 5/1992 | Walters | 364/413.17 |
| 5,123,037 A | | 6/1992 | Picard | 378/99 |
| 5,402,338 A | * | 3/1995 | Ito | 600/407 |
| 5,748,705 A | * | 5/1998 | Stein et al. | 378/196 |
| 5,910,972 A | * | 6/1999 | Ohkubo et al. | 378/54 |
| 6,058,322 A | * | 5/2000 | Nishikawa et al. | 600/408 |
| 6,205,348 B1 | * | 3/2001 | Giger et al. | 600/407 |
| 6,240,201 B1 | | 5/2001 | Xu et al. | 382/130 |
| 2001/0010732 A1 | * | 8/2001 | Oosawa | 382/128 |
| 2002/0172403 A1 | * | 11/2002 | Doi et al. | 382/128 |
| 2003/0142787 A1 | * | 7/2003 | Jabri et al. | 378/98.12 |

FOREIGN PATENT DOCUMENTS

EP    1005832 A    6/2000

* cited by examiner

*Primary Examiner*—Matthew C. Bella
*Assistant Examiner*—Patrick L. Edwards
(74) *Attorney, Agent, or Firm*—Cantor Colburn LLP

(57) ABSTRACT

A method, system, and storage medium for computer aided processing of dual or multiple energy images includes employing a data source, the data source including a dual or multiple energy image set, defining a region of interest within one or more images from the dual or multiple energy image set, extracting a set of feature measures from the region of interest, and employing a feature extraction algorithm on the feature measures for identifying an optimal set of features. The method may be employed for identifying bone fractures, disease, obstruction, or any other medical condition.

40 Claims, 9 Drawing Sheets

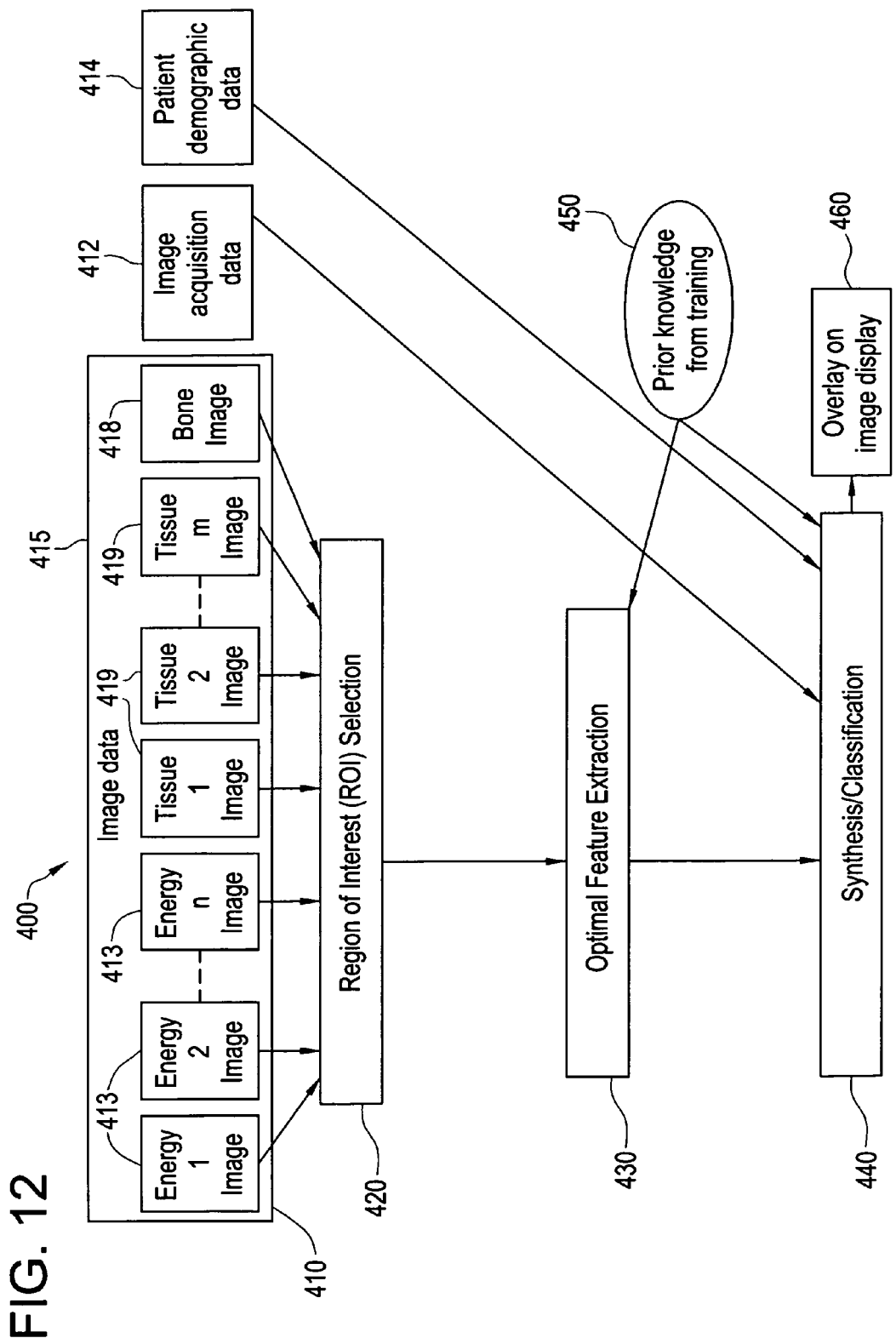

COMPUTER AIDED DIAGNOSIS FROM MULTIPLE ENERGY IMAGES

BACKGROUND OF INVENTION

This invention generally relates to computer aided detection and diagnosis (CAD) of radiographic images. More particularly, this invention relates to a method and system for computer aided detection and diagnosis of dual energy ("DE") or multiple energy images.

The classic radiograph or "X-ray" image is obtained by situating the object to be imaged between an X-ray emitter and an X-ray detector made of photographic film. Emitted X-rays pass through the object to expose the film, and the degree of exposure at the various points on the film are largely determined by the density of the object along the path of the X-rays.

It is now common to utilize solid-state digital X-ray detectors (e.g., an array of switching elements and photo-sensitive elements such as photodiodes) in place of film detectors. The charges generated by the X-rays on the various points of the detector are read and processed to generate a digital image of the object in electronic form, rather than an analog image on photographic film. Digital imaging is advantageous because the image can later be electronically transmitted to other locations, subjected to diagnostic algorithms to determine properties of the imaged object, and so on.

Dual energy (DE) imaging in digital X-Ray combines information from two sequential exposures at different energy levels, one with a high energy spectrum and the other with a low energy spectrum. With a digital X-ray detector, these two images are acquired sequentially to get two additional images, a soft tissue image and a bone image. A multiple energy imaging system can be built that can be used to further decompose the bone and tissues in an anatomy. A series of images at different energies/kVps (Energy 1, . . . Energy n) can be acquired in a rapid sequence and decomposed into bone and different tissue types (Tissue 1, . . . Tissue m).

Diagnosis from radiographic images has traditionally been a visual task. Due to the subjective nature of the task, the diagnosis is subject to inter- and intra-reader variability. In addition, due to the underlying and overlying structures relevant to the pathologies of interest, visual assessment can be difficult. Subtle rib fractures, calcifications, and metastatic bone lesions (metastases) in the chest can be difficult to detect on a standard chest X-ray. As an additional example, only 5-25% of pulmonary nodules are detected today with chest radiographs, but 35-50% are visible in retrospect.

SUMMARY OF INVENTION

The above discussed and other drawbacks and deficiencies are overcome or alleviated by a method, system, and storage medium for computer aided processing of dual or multiple energy images. The method usable in the system and implemented by a computer via the storage medium includes employing a data source, the data source including a dual or multiple energy image set, defining a region of interest within an image from the dual or multiple energy image set, extracting a set of feature measures from the region of interest, and employing a feature extraction algorithm on the feature measures for identifying an optimal set of features from the region of interest. The method may be employed for identifying a bone fracture, nodule, disease, obstruction, or any other medical condition.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several FIGS..

DETAILED DESCRIPTION

Figure 1:
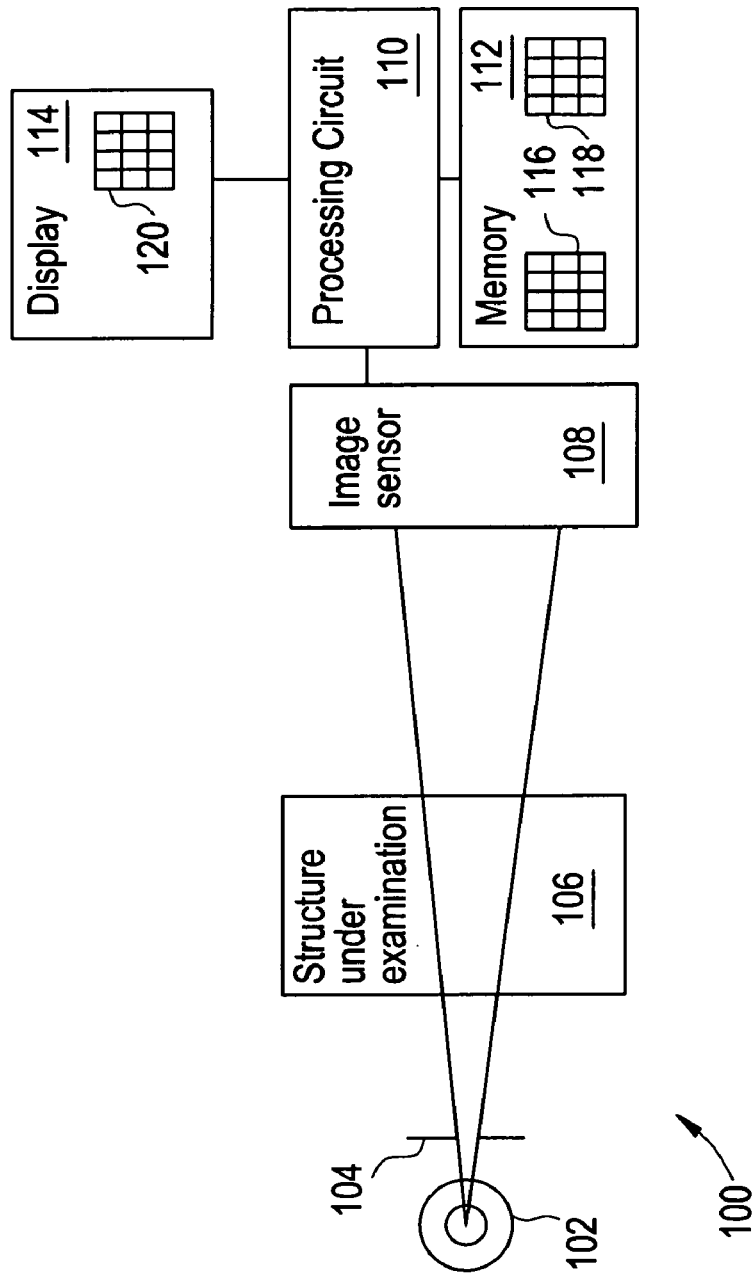
FIG. 1 is a block diagram of an exemplary X-ray imaging system.

FIG. 1 illustrates an exemplary X-ray imaging system 100. The imaging system 100 includes an X-ray source 102 and a collimator 104, which subject structure under examination 106 to X-ray photons. As examples, the X-ray source 102 may be an X-ray tube, and the structure under examination 106 may be a human patient, test phantom or other inanimate object under test. The X-ray source 102 is able to generate photons at a first energy level and at least a second energy level different than the first energy level. Multiple, more than two, energy levels are also within the scope of this method and system.

The X-ray imaging system 100 also includes an image sensor 108 coupled to a processing circuit 110. The processing circuit 110 (e.g., a microcontroller, microprocessor, custom ASIC, or the like) is coupled to a memory 112 and a display 114. The display 114 may include a display device, such as a touch screen monitor with a touch-screen interface. As is known in the art, the system 100 may include a computer or computer-like object which contains the display 114. The computer or computer-like object may include a hard disk, or other fixed, high density media dives, connected using an appropriate device bus, such as a SCSI bus, an Enhanced IDE bus, a PCI bus, etc., a floppy drive, a tape or CD ROM drive with tape or CD media, or other removable media devices, such as magneto-optical media, etc., and a mother board. The motherboard includes, for example, a processor, a RAM, and a ROM, I/O ports which are used to couple to the image sensor 108, and optional specialized hardware for performing specialized hardware/software functions, such as sound processing, image processing, signal processing, neural network processing, etc., a microphone, and a speaker or speakers. Associated with the computer or computer-like object may be a keyboard for data entry, a pointing device such as a mouse, and a mouse pad or digitizing pad. Stored on any one of the above-described storage media (computer readable media), the system and method include programming for controlling both the hardware of the computer and for enabling the computer to interact with a human user. Such programming may include, but is not limited to, software for implementation of device drivers, operating systems, and user applications. Such computer readable media further includes programming or software instructions to direct the general purpose computer to performance in accordance with the system and method. The memory 112 (e.g., including one or more of a hard disk, floppy disk, CDROM, EPROM, and the like) stores a high energy level image 116 (e.g., an image read out from the image sensor 108 after 110-140 kVp 5 mAs exposure) and a low energy level image 118 (e.g., an image read out after 70 kVp 25 mAs exposure). Processing circuit 110 provides an image 120 for display on device 114. As described in further detail herein, the image 120 may be representative of different structures (e.g., soft-tissue, bone). The image sensor 108 may be a flat panel solid state image sensor, for example, although conventional film images stored in digital form in the memory 112 may also be processed as disclosed below as well.

Figure 2:
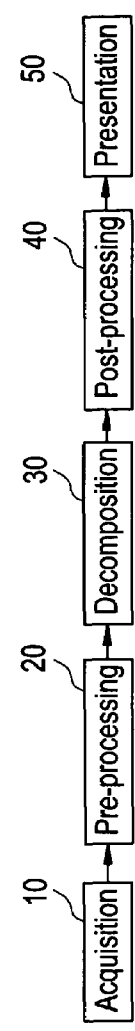
FIG. 2 is a high-level flowchart of an exemplary image acquisition and processing process.
Figure 3:
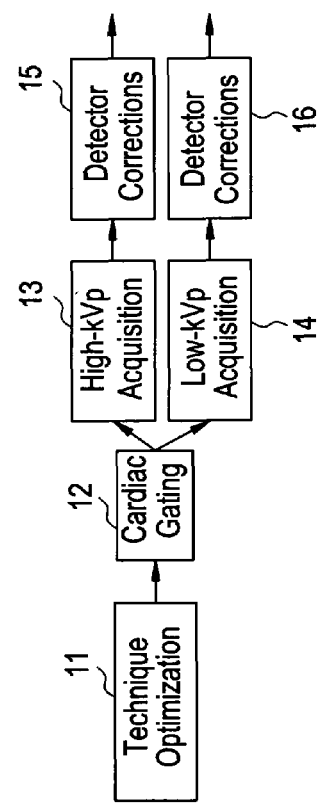
FIG. 3 is a flowchart of exemplary image acquisition processing.
Figure 4:
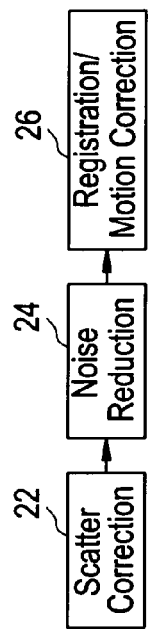
FIG. 4 is a flowchart of exemplary image pre-processing.

Referring to FIG. 2, once the acquisition step 10 is completed, flow proceeds to step 20 where the acquired images are pre-processed. FIG. 4 is flowchart of an exemplary pre-processing routine. The pre-processing includes a scatter correction step 22 which may be implemented in software and/or hardware. The scatter correction routine may be applied to each image individually or utilize common information from both the high kVp and the low kVp images to reduce scatter. Existing scatter correction techniques may be used such as hardware solutions including specialized anti-scatter grids, and or software solutions using convolution-based or deconvolution-based methods. Additionally, software techniques can utilize information from one image to tune parameters for the other image. Scatter correction addresses decomposition artifacts due to x-ray scatter.

Once scatter correction is performed, noise reduction is performed at step 24 where one or more existing noise reduction algorithms are applied to the high kvp and the low kVp images, either individually or simultaneously. The noise correction addresses increased noise that may result from the DE decomposition. At step 26, registration is performed to reduce motion artifacts by correcting for motion and aligning anatomies between the high kVp and the low kVp images. The registration algorithms may be known rigid-body or warping registration routines applied to the high kVp and the low kVp images. Alternatively, the techniques may be iterative and make use of the additional information in decomposed soft-tissue and bone images developed at step 30. The registration processing addresses residual structures in the soft-tissue image and/or the bone image and lung/heart motion artifacts.

Referring to FIG. 2, once the pre-processing step 20 is completed, flow proceeds to step 30 where the acquired images are decomposed to generate a raw soft-tissue image and a raw bone image. A standard image (also referred to as a standard posterior-anterior (PA) image) is also defined based on the high kVp image. The decomposition may be performed using known DE radiography techniques. Such techniques may include log-subtraction or basis material decomposition to create raw soft-tissue and raw bone images from the high-energy and low-energy acquisitions. Information from the raw soft-tissue image and raw bone image may be used in the registration/motion correction step 26. For example, edge information and/or artifact location information can be derived from the decomposed images for use in the registration/motion correction.

Figure 5:
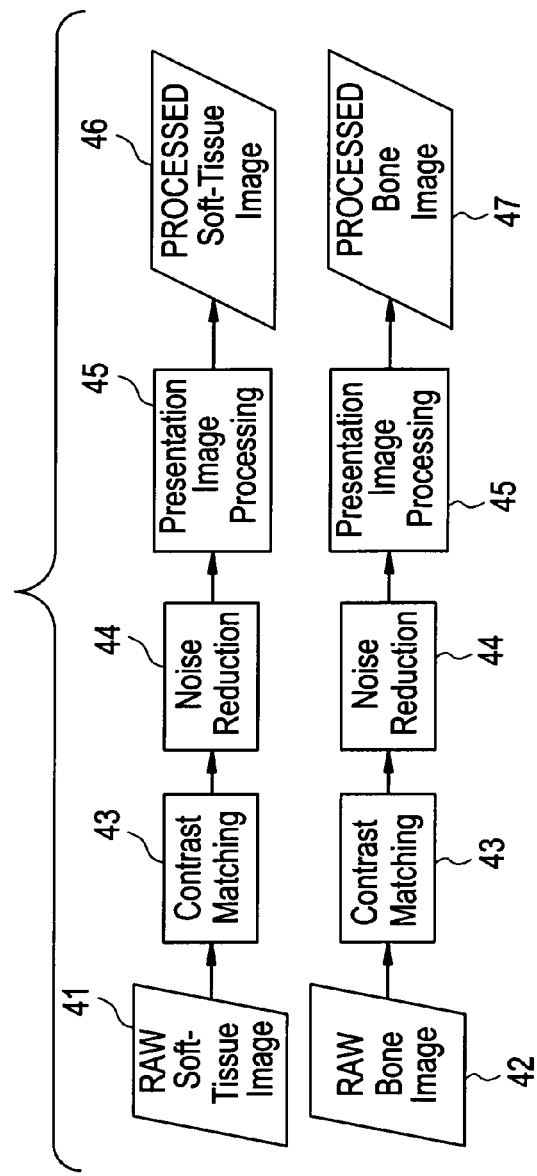
FIG. 5 is a flowchart of exemplary image post-processing.

Referring to FIG. 2, once the decomposition step 30 is completed, flow proceeds to step 40 where the acquired images are post-processed. FIG. 5 is a flowchart of an exemplary post-processing routine. As shown in FIG. 5, the raw soft-tissue image 41 and the raw bone image 42 are subjected to similar processing. Contrast matching 43 is performed match contrast of structures in raw soft-tissue image 41 and the raw bone image 42 to the corresponding structures in a standard image. For example, contrast of soft-tissue structures in raw soft-tissue image 41 (e.g., chest image) is matched to the contrast in the standard PA image. The contrast matching is performed to facilitate interpretation of the x-ray images.

At 44, one or more noise reduction algorithms may be applied to the soft-tissue image 41 and the bone image 42. Existing noise reduction algorithms may be used. The noise reduction addresses noise due to DE decomposition. At 45, presentation image processing may be performed to the soft-tissue image 41 and the bone image 42. The presentation processing includes processes such as edge enhancement, display window level and window width adjustments for optimal display. The result of the post-processing 40 is depicted as processed soft-tissue image 46 and processed bone image 47.

Referring to FIG. 2, once the post-processing step 40 is completed, flow proceeds to step 50 where the acquired images are processed for display.

Computer-aided algorithms have the potential of improving accuracy and reproducibility of disease detection when used in conjunction with visual assessment by radiologists. Computer-aided algorithms can be used for detection (presence or absence) or diagnosis (normal or abnormal). The detection or diagnosis is performed based upon knowledge acquired by training on a representative sample database. The sample data in the database and the features of the data that the algorithms are trained are two important aspects of the training process that affect the performance of CAD algorithms. The accuracy of the CAD algorithms improves with improvements on the information it is trained on. With conventional radiographs, overlying and underlying structures confound the relevant information making diagnosis or detection difficult even for computerized algorithms. The method and system described herein addresses this problem by using dual energy images, in particular, in conjunction with conventional radiographic images for CAD. In particular, this method combines information from four images to aid computerized detection algorithms.

Figure 6:
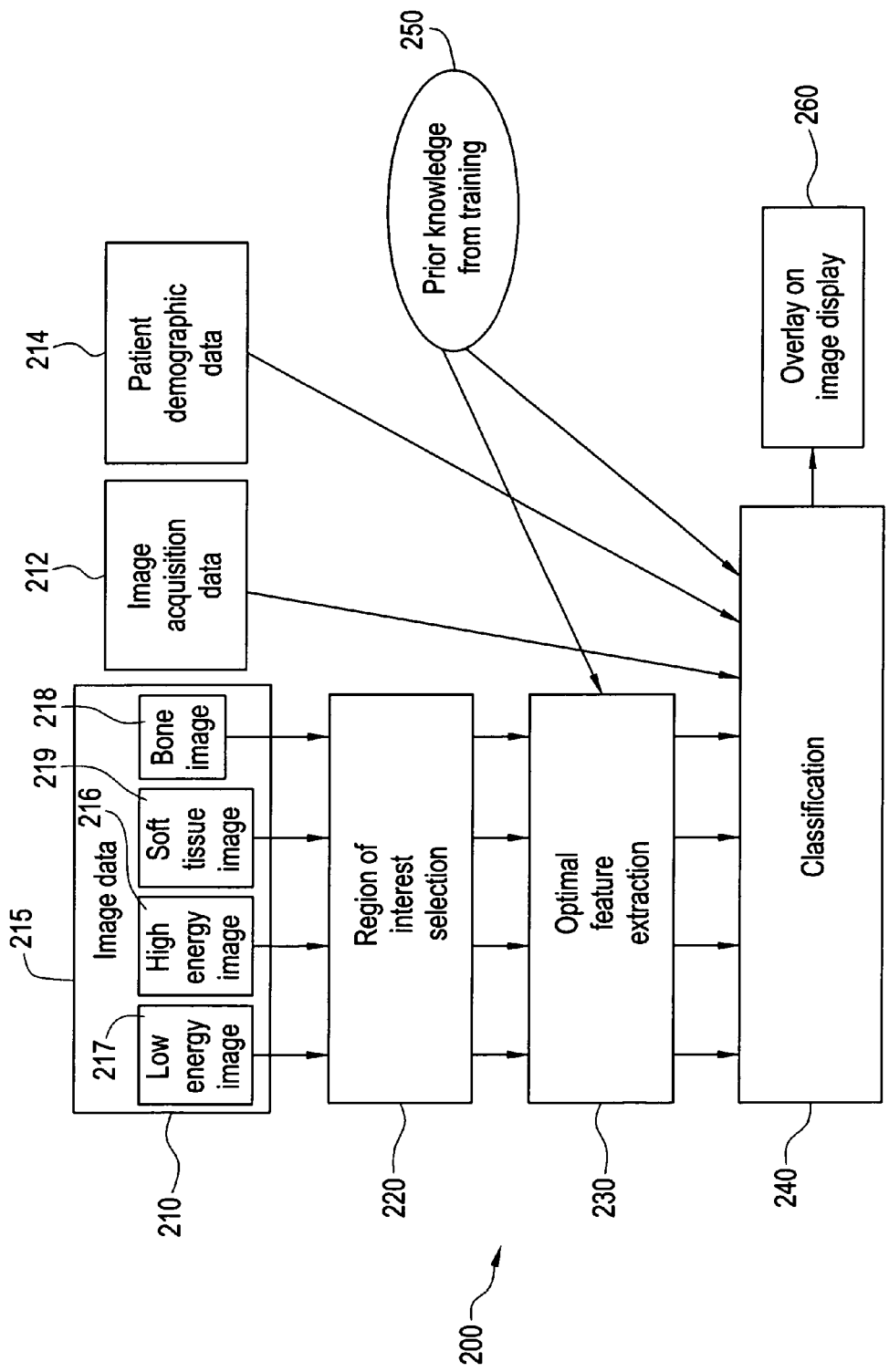
FIG. 6 is a flowchart of a computer aided process of detection and diagnosis of dual energy images.

As shown in FIG. 6 the dual energy CAD system 200 has several parts including a data source 210, a region of interest 220, optimal feature selection 230, and classification 240, training 250, and display of results 260.

Figure 7:
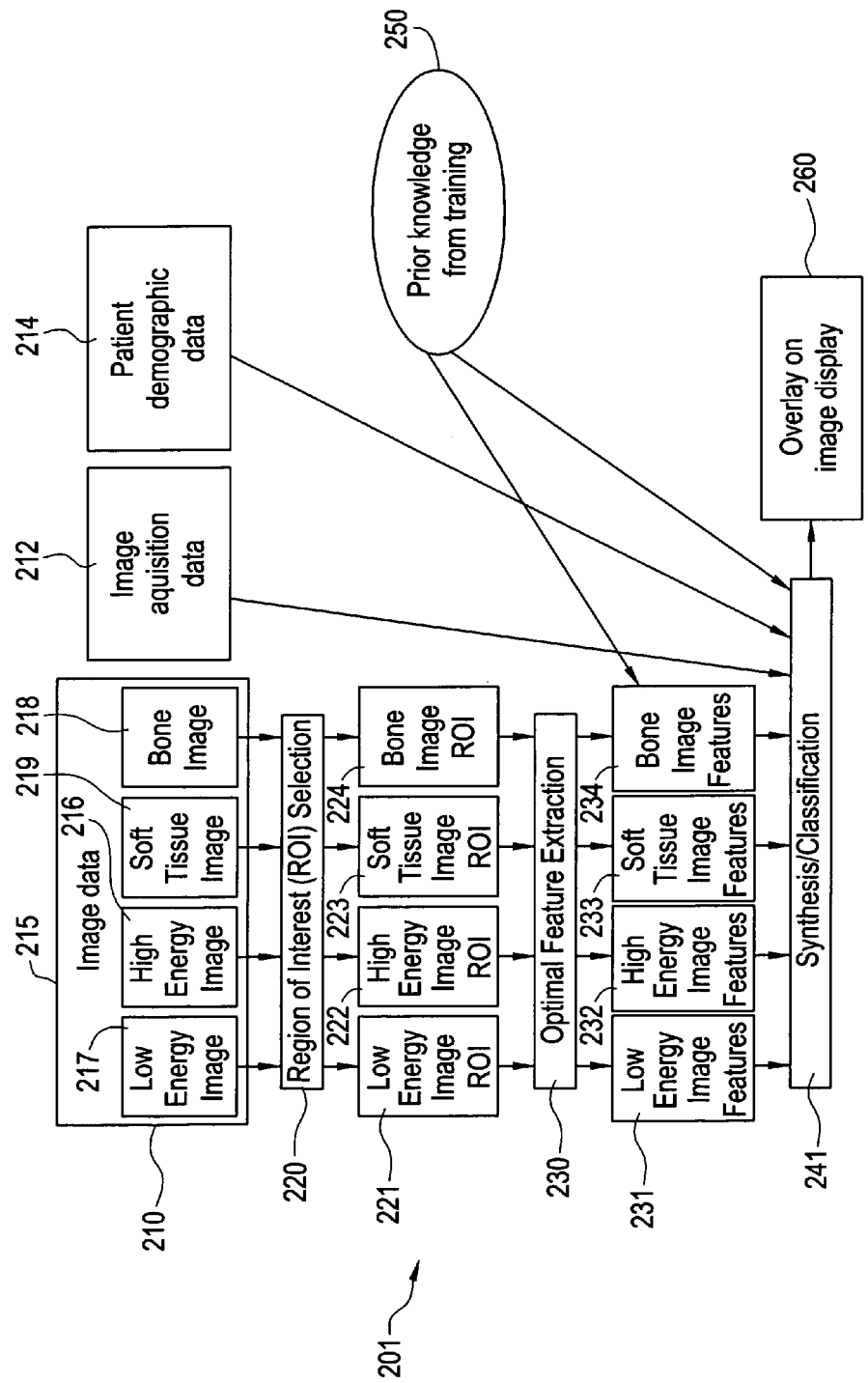
FIG. 7 is a flowchart of another computer aided process of detection and diagnosis of dual energy images.

It should be noted here that dual energy CAD 200 be performed once by incorporating features from all images 215 or can be performed in parallel. As shown in FIG. 7, the parallel operation for a dual energy CAD 201 would involve performing CAD operations, as described in FIG. 6, individually on each image 216, 217, 218, 219 and combining the results of all CAD operations in a synthesis/classification stage 214. That is, the ROI selection 220 can be performed on each image 216, 217, 218, and 219 to provide a low energy image ROI 221, a high energy image ROI 222, a soft tissue image ROI 223, and a bone image ROI 224. Likewise, the optimal feature extraction stage 230 can be performed on each image ROI 221, 222, 223, and 224 to result in low energy image features 231, high energy image features 232, soft tissue image features 233, and bone image features 234. At the synthesis/classification stage 241, the results of all of the CAD operations can be combined. Thus, FIGS. 6 and 7 show two different methods of performing dual energy CAD, however other methods are also within the scope of this invention such as the ROI selection stage 220 performing in parallel as shown in FIG. 7, but the feature extraction stage 230 performing on a combined ROI such as shown in FIG. 6. In addition, CAD operations to detect multiple diseases, fractures, or any other medical condition can be performed in series or parallel.

Referring now to either FIG. 6 or 7, for the data source 210, data may be obtained from a combination of one or more sources. Image acquisition system information 212 such as kVp (peak kilovoltage, which determines the maximum energy of the X-rays produced, wherein the amount of radiation produced increases as the square of the kilovoltage), mA (the X-ray tube current is measured in milliamperes, where 1 mA=0.001 A), dose (measured in Roentgen as a unit of radiation exposure, rad as a unit of absorbed dose, and rem as a unit of absorbed dose equivalent), SID (Source to Image Distance), etc., may contribute to the data source 210. Patient demographics/symptoms/history 214 such as smoking history, sex age, and clinical symptoms may also be a source for data 210. Dual energy image sets 215 (high energy image 216, low energy image 217, bone image 218, soft tissue image 219) are an additional source of data for the data source 210.

On the image-based data 215, a region of interest 220 can be defined from which to calculate features. The region of interest 220 can be defined several ways. For example, the entire image 215 could be used as the region of interest 220. Alternatively, a part of the image, such as a candidate nodule region in the apical lung field could be selected as the region of interest 220. The segmentation of the region of interest 220 can be performed either manually or automatically. The manual segmentation may involve displaying the image and a user delineating the area using, for example, a mouse. An automated segmentation algorithm can use prior knowledge such as the shape and size to automatically delineate the area of interest 220. A semi-automated method which is the combination of the above two methods may also be used.

Figure 8:
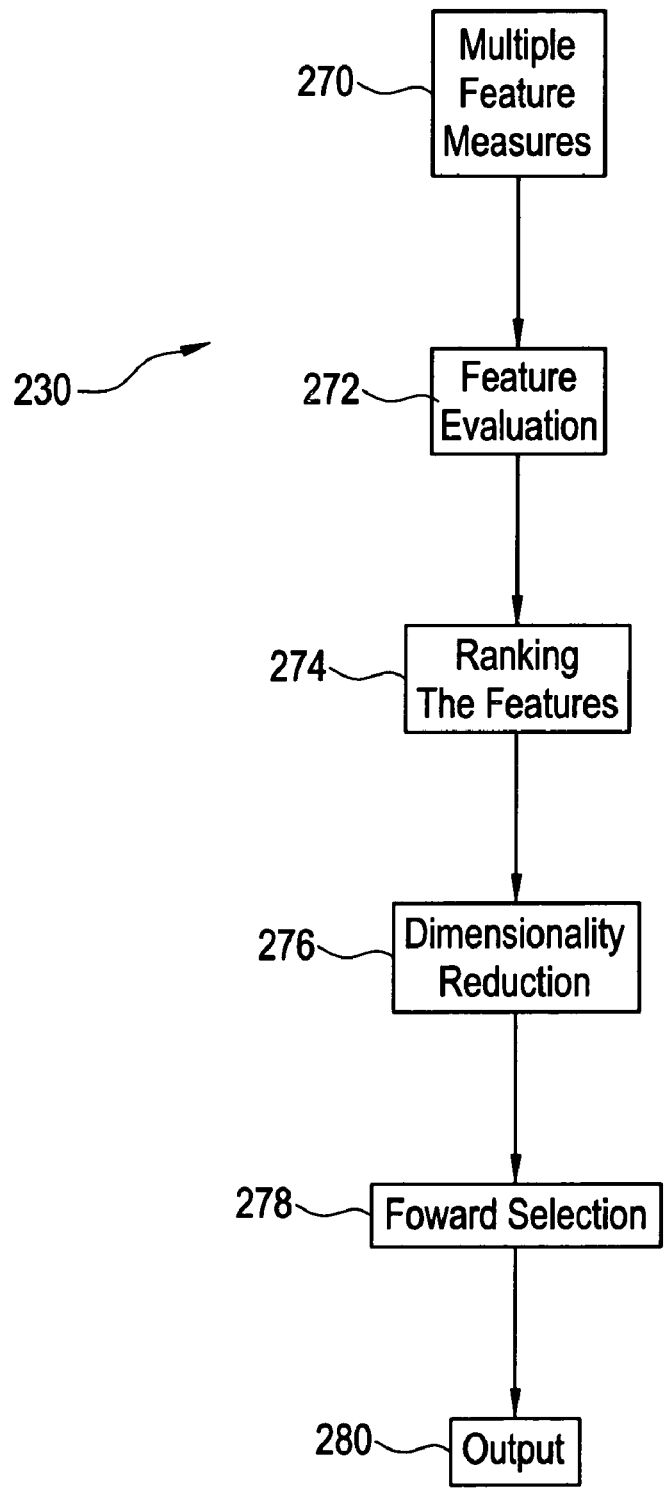
FIG. 8 is flowchart of an exemplary feature selection algorithm for use in the computer aided process of FIGS. 6 and 7.

The feature selection algorithm 230 is then employed to sort through the candidate features and select only the useful ones and remove those that provide no information or redundant information. With reference to FIG. 8, the feature extraction process, or optimal feature extraction 230, involves performing computations on the data sources 210. For example, on the image-based data 215, the region of interest statistics such as shape, size, density, curvature can be computed. On acquisition-based 212 and patient-based 214 data, the data 212, 214 themselves may serve as the features. As further shown in FIG. 8, the multiple feature measures 270 from the high energy image, low energy image, soft image, and bone images or a combination of those images are extracted, for example measured features such as shape, size, texture, intensity, gradient, edge strength, location, proximity, histogram, symmetry, eccentricity, orientation, boundaries, moments, fractals, entropy, etc., patent history such as age, gender, smoking history, and acquisition data such as kVp and dose. The term "feature measures" thus refers to features which are computed, features which are measured, and features which just exist. A large number of feature measures are included, however the method ensures that only the features which provide relevant information are maintained. Step 272 within the feature selection algorithm 230 refers to feature evaluation 272 in terms of its ability to separate the different classification groups using, for example, distance criteria. Distance criteria will evaluate how well, using a particular feature, the method can separate the different classes that are used. Several different distance criteria can be used such as divergence, Bhattacharya distance, Mahalanobis distance. These techniques are described in "Introduction to Statistical Pattern Recognition", K. Fukanaga, Academic Press, $2^{nd}$ ed., 1990, which is herein incorporated by reference. Step 274 ranks all the features based on the distance criteria. That is, the features are ranked based on their ability to differentiate between different classes, their discrimination capability. The feature selection algorithm 230 is also used to reduce the dimensionality from a practical standpoint, where the computation time might be too long if the number of features to compute is large. The dimensionality reduction step 276 refers to how the number of features are reduced by eliminating correlated features. Extra features which are merely providing the same information as other features are eliminated. This provides a reduced set of features which are used by the forward selection step 278 which selects the highest ranked features and then adding additional features, based on a descending ranking, until the performance no longer improves. That is, no more features are added when the point is reached where adding additional features no longer provides any useful information. At this point, the output 280 provides an optimal set of features.

Figure 9:
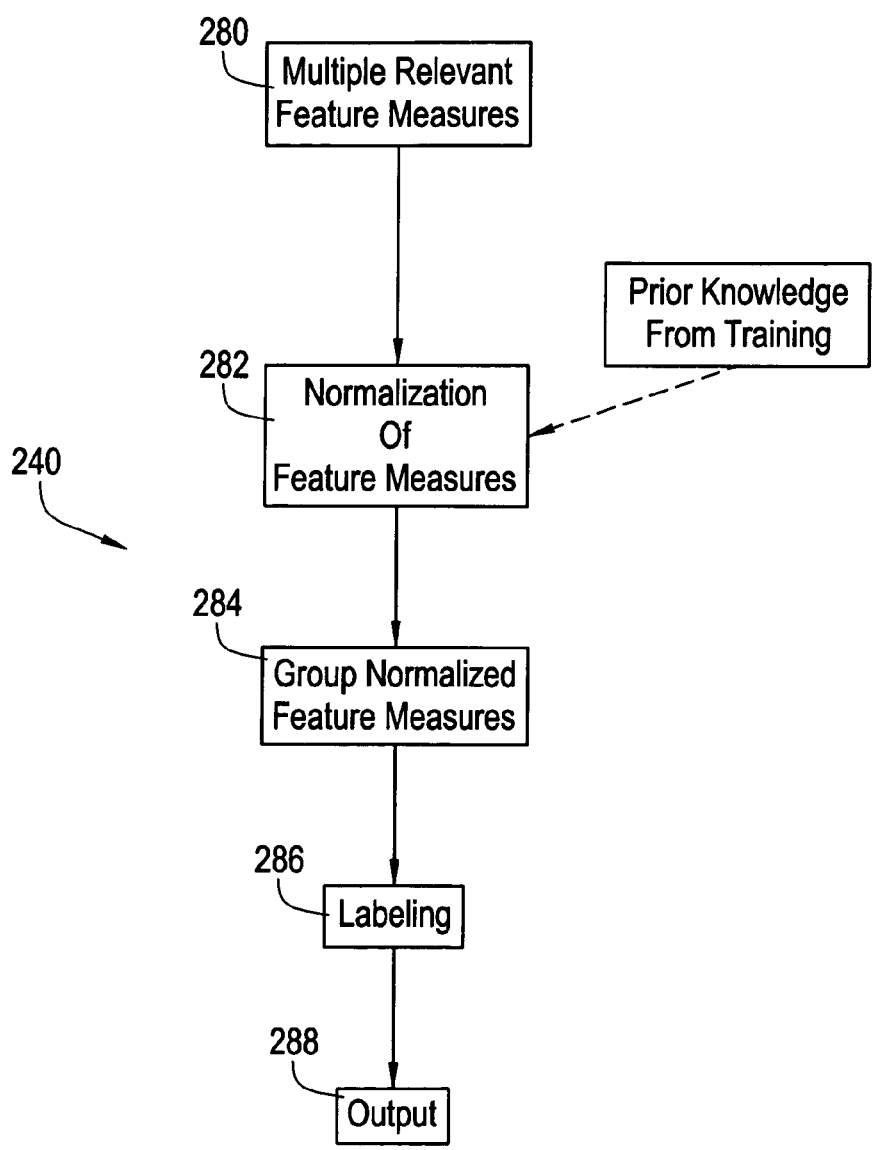
FIG. 9 is a flowchart of an exemplary classification algorithm for use in the computer aided process of FIGS. 6 and 7.

Once the features, such as shape, size, density, gradient, edges, texture, etc., are computed as described above in the feature selection algorithm 230 and an optimal set of features 280 is produced, a pre-trained classification algorithm 240 can be used to classify the regions of interest 220 into benign or malignant nodules, calcifications, fractures or metastases, or whatever classifications are employed for the particular medical condition involved. With reference to FIG. 9, the set of features 280 is used as the input to the classification algorithm 240. In step 282, the normalization of the feature measures from set 280 is performed with respect to feature measures derived from a database of known normal and abnormal cases of interest. This is taken from the prior knowledge from training 250. The prior knowledge from training may contain, for example, examples of features of confirmed malignant nodules and examples of features of confirmed benign nodules. The training phase 250 may involve, for example, the computation of several candidate features on known samples of benign and malignant nodules. Step 284 refers to grouping the normalized feature measures. Several different methods can be used such as Bayesian classifiers (an algorithm for supervised learning that stores a single probabilistic summary for each class and that assumes conditional independence of the attributes given the class), neural networks (which works by creating connections between processing elements whereby the organization and weights of the connections determine the output; neural networks are effective for predicting events when the networks have a large database of prior examples to draw on, and are therefore useful in image recognition systems and medical imaging), rule-based methods (which use conditional statements that tells the system how to react in particular situations), fuzzy logic (which recognizes more than simple true and false values), clustering techniques, and similarity measure approach. Such techniques are described in "Fundamentals of Digital Image Processing" by Anil K. Jain, Prentice Hall 1988, herein incorporated by reference. Once the normalized feature measures have been grouped, then the classification algorithm 240 labels the feature clusters in step 286 and outputs in step 288 a display of the output.

Dual-energy techniques enable the acquisition of multiple images for review by human or machine observers. CAD techniques could operate on one or all of the images 216, 217, 218, and 219, and display the results 260 on each image 216, 217, 218, and 219, or synthesize the results for display 260 onto a single image 215. This would provide the benefit of improving CAD performance by simplifying the segmentation process, while not increasing the quantity of images to be reviewed. This display of results 260 forms part of the presentation phase 50 shown in FIG. 2.

Following identification 230 and classification 240 of a suspicious candidate region, its location and characteristics must be displayed to the radiologist or reviewer of the image. In non-dual-energy CAD applications this is done through the superposition of a marker, for example an arrow or circle, near or around the suspicious lesion. Dual-energy CAD affords the ability to display markers for computer detected (and possibly diagnosed) nodules on any of the four images (high energy image 216, low energy image 217, bone image 218, soft tissue image 219). In this way, the reviewer may view only a single image 215 upon which is superimposed the results from an array of CAD operations 200. The CAD system 201 synthesizes the results in step 241 when the images are processed separately as shown in FIG. 7. Each CAD operation (defined by a unique segmentation (ROI) 220, feature extraction 230, and classification procedure 240 or 241) may be represented by a unique marker style.

An example of such a dual energy CAD display will be described for lung cancer chest imaging. Let us assume that a patient has a dual-energy exam (as described with reference to FIGS. 1-5) that is then processed with a dual-energy CAD system 200 or 201. A CAD operation identifies two suspicious lesions characteristic of malignancy on the soft-tissue image 219. On the bone-image 218, a CAD operation identifies a calcified nodule (indicating a benign process), and a bone lesion. At the synthesis stage, which may form part of the classification process when either or both of the ROI and feature extraction stages apply to each image, the classification 240 takes these results and determines that one of the soft-tissue nodules is the same as the calcified nodule apparent on the bone-image 218. The reviewer would then be presented with the high energy image 216, a first image taken with a technique to mimic what is currently standard practice for single-energy chest radiography. The reviewer would also be presented with a second image, the same image as the first image but with markers indicating the results of the CAD operations 220, 230, 240 superimposed on the image data. This second image could be simultaneously displayed on a second hard-or soft-copy image display, or toggled with the other images via software on a soft-copy display. Superimposed upon the second image may be, for example, circles around the suspicious lung nodule classified as having characteristics of malignancy, a square around the calcified lung nodules classified as benign, and an arrow pointing to the detected bone lesions. In this manner, the reviewer gets the benefit of the information from CAD operations 200 on each image presented simultaneously for optimal review.

These methods 200, 201 improve the performance of computer-aided detection or diagnosis algorithms by providing input data with overlying structures removed. Also, since the imaged anatomy is separated based on tissue type (soft tissue or bone), this algorithm 200 has the potential of extracting more diagnostic features per anatomy than with standard radiography.

Previous CR (computed radiography) dual-energy images are of rather poor quality and noisy compared to the standard radiology image and thus computer-aided algorithms have not been previously employed on such images. This system and method 200, 201 uses information from high energy image 216, low-energy image 217, soft-tissue image 219, and bone images 218 in addition to acquisition parameters 212 and patient information 214. Furthermore, the results can be displayed to the reviewer without increasing the number of images over that of conventional CAD techniques.

The above-described method 200, 201 can additionally be utilized for identification of calcifications, rib fractures and metastatic bone lesions. By providing a bone image 218 with no over/underlying soft-tissue, DE imaging creates an effective opportunity for automatic detection and classification of subtle bone fractures, calcifications and metastases that might otherwise be missed by the standard image reader.

Figure 10:
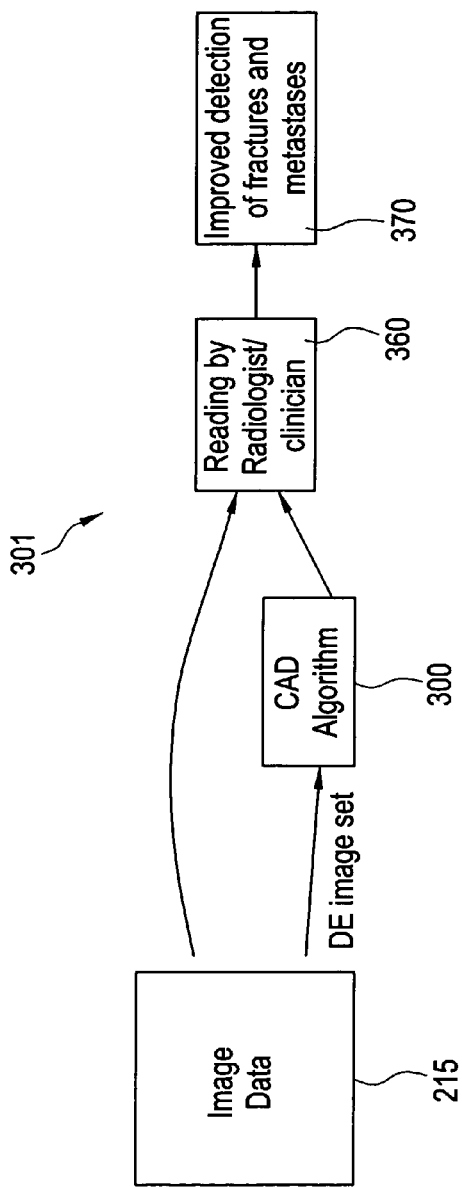
FIG. 10 is a flowchart of a computer aided process of detecting calcifications, fractures and metastases in a bone image.
Figure 11:
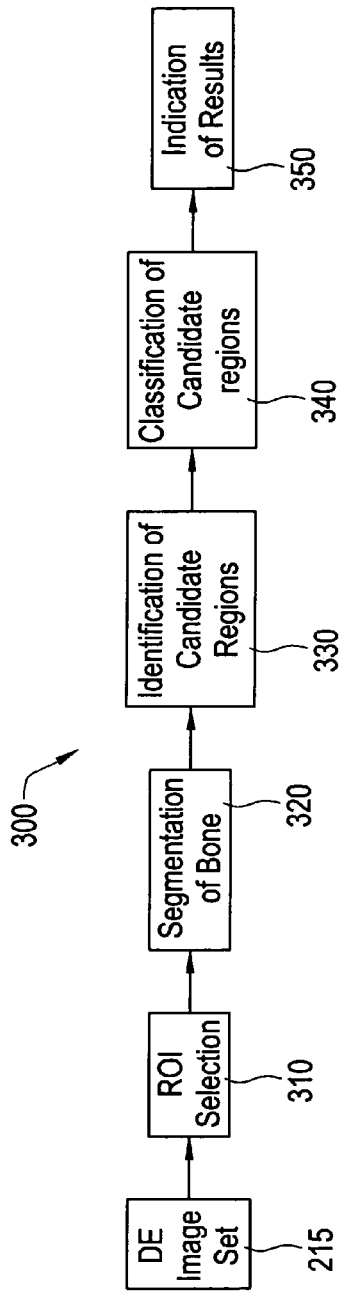
FIG. 11 is a flowchart of a computer aided algorithm for use in the process of FIG. 10; and, FIG. 12 is a flowchart of a computer aided process of detection and diagnosis of multiple energy images.

Turning now to FIGS. 10 and 11, a diagrammed example of the methods 200, 201 is shown. The method 301 uses a dual energy computer-aided detection/diagnosis (CAD) algorithm 300 for segmenting the bone from the background and detecting/identifying candidate bone regions with possible calcifications, fractures or metastases. These candidate regions are then classified based on features extracted from the corresponding complete image set 215 (high-energy 216, low-energy 217, bone 218, and soft-tissue 219). The classification stage not only rules out what it considers false positives, but can also provide additional information about the fracture or lesion (fracture type, lesion size, etc.) The results are then highlighted on the images for the reader to assess.

As shown in FIG. 11, the first step in a CAD algorithm 300 for detecting calcifications, rib fractures and metastases in DE images 215 requires the selection of the desired area to search, or selection of the region of interest (ROI) 310. In a dual energy chest exam, this would typically consist of the entire image, but could certainly consist of a smaller region of interest if a specific region were suspected. The selection of the region of interest (ROI) 310 can be done manually or by automated algorithms based on user specifications as described above with reference to ROI 220.

Next, segmentation of bone 320 occurs. The purpose of the segmentation 320 is to separate the bone from the background (non-bone). One embodiment would be a region-growing algorithm. Manual or automated methods can be used for initializing region growing. In manual methods, a means is provided for the user to select the seed point(s). In automated methods, attributes of the bone such as intensity range, gradient range, shape, size etc. can be used for initializing seed points. Another potential segmentation method would involve multi-level intensity thresholding.

Then, candidate regions can be identified in step 330. One method for identifying candidate regions is based on an edge detection algorithm. To eliminate noise and false edges, image processing using morphological erosion could follow. In addition, to rule out longer lines that are most likely rib edges, a connectivity algorithm could be applied. Therefore, the remaining image consists of only those edges that are possible candidates for the calcifications, fractures and metastases.

Candidate regions may then be classified in step 340. The classification of the remaining candidate regions may comprise of a rule-based approach. The rules can be different for identification of calcifications, metastases and fractures. There will preferably be different rules for the different types of fractures, and different rules for the different properties of metastases. For example, for fractures, one might wish to separate the edges inside the ribs from the edges outside the ribs, as edges inside the ribs are candidates for fractures. Rules could also be based on size measurements of the line edges.

Remaining candidate regions should then be indicated to the user or reader for inspection in a presentation step, or indication of results 350. This could be performed by highlighting areas on the original bone image, either with arrows, circles, or some other indicator or marker. Additional information such as fracture type or lesion size can also be overlaid on the images.

Referring again to FIG. 10, the indication of results 350 may then be read by a radiologist or clinician in step 360 and this method 301 can be used to improve the detection of calcifications, subtle rib fractures and metastatic bone lesions in chest radiography as exemplified by step 370. The detection of such ailments can lead to increased benefit to the patient by early detection, leading to improved patient care by the clinician. The ability to provide a bone image without over/underlying soft-tissue can also be used to greatly improve detection and diagnosis of bone-related pathology. Using the bone image for calcifications, fracture and metastases detection is a diagnostic concept for DE imaging which has not previously been available.

While specific examples including lung cancer chest imaging and detection of calcifications, rib fractures and metastases have been described, it should be understood that the methods and systems described above could be employed for detecting and/or diagnosing any medical condition, obstruction, or disease involving any part of the body.

Also, while DE imaging has been specifically addressed, it is further within the scope of this invention to employ the above-described methods on multiple energy images. For example, a multiple energy imaging system 400 is shown in FIG. 12, which is similar to the DE imaging systems 200, 201, and 300 as described above in that in includes a data source 410 including image data 415, image acquisition data 412, and patient demographic data 414, defining or selecting a region of interest 420, optimal feature extraction 430, synthesis/classification 440, and overlay on image display 460. Also as in the previously described DE imaging systems, prior knowledge from training 450 is applied to the optimal feature extraction stage 430 and the synthesis/classification stage 440. Thus, the only distinction between the method 400 and the previously described DE methods is the content of the image data 415. That is, while the DE methods utilize a high energy image, a low energy image, a soft tissue image and a bone image, the multiple energy imaging system 400 uses a series of images 413 taken at different energies/kVps (Energy 1 image, Energy 2 image, . . . Energy n image). These images 413 can be acquired in a rapid sequence and decomposed into a bone image 418 and different tissue type images 410 (Tissue 1 image, Tissue 2 image, . . . Tissue m image). Information from one or more of these images can be used to detect and diagnose various diseases or medical conditions. As an example, if a certain disease needs to be detected, regions of interest can be identified and features can be computed on Tissue 3 image and the Energy 1 image. For a different disease type, all the images may be used. As in the DE energy imaging systems, region of interest selection, optimal feature computation, and classification may be performed in series or in parallel on the image data 415. For the purposes of this specification, it should be noted that "multiple" energy image encompasses dual energy imaging, since two images are multiple images.

It should be noted that the methods 200, 201, 300, and 400 may be employed within the imaging system 100, and in particular, may be stored within memory 112 and processed by processing circuit 110. It is further within the scope of this invention that the disclosed methods may be embodied in the form of any computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for computer aided processing of dual or multiple energy images, the method comprising:

employing a data source, the data source including a dual or multiple energy image set, the image set comprising four distinct images comprising a high energy image, a low energy image, a bone image, and a soft tissue image, each member of the image set being useable for feature detection computer aided processing together with each other member of the image set, each member of the image set being arranged at the data source in such a manner as to allow the computer aided processing to be performed once by incorporating features from all images of the image set;

processing the image set by utilizing all of the four distinct images together according to the following:

receiving as inputs features from all of the four images of the image set, the features comprising computed features, measured features, or both;

defining a region of interest within an image from the dual or multiple energy image set;

combining information from all of the four images;

extracting a set of feature measures from the region of interest; and, reporting the feature measures on the region of interest.

2. The method of claim 1 further comprising employing a feature selection algorithm on the region of interest and classifying the region of interest.

3. The method of claim 2 further comprising incorporating prior knowledge from training for classifying the region of interest.

4. The method of claim 3 wherein incorporating prior knowledge from training includes computing features on known samples of different normal and pathological medical conditions.

5. The method of claim 4 wherein the feature selection algorithm sorts through the features of known samples, selects useful features of known samples, and discards features of known samples which do not provide useful information.

6. The method of claim 2 wherein classifying the region of interest using the optimal set of features comprises classifying one or more medical conditions.

7. The method of claim 2, wherein the feature selection algorithm comprises:

ranking each feature measure coming from the data source;

reducing a quantity of feature measures by eliminating correlated features, thereby eliminating extra features that provide the same information as other features, resulting in a reduced set of feature measures; and selecting a highest ranked feature measure, and adding additional feature measures, based on a descending ranking, until the adding of the additional feature measures no longer provides additional useful information.

8. The method of claim 1 wherein processing dual or multiple energy images comprises detecting and diagnosing one or more medical conditions.

9. The method of claim 1 wherein defining a region of interest comprises manually selecting a region of interest.

10. The method of claim 1 wherein defining a region of interest comprises utilizing an automated algorithm with or without user specifications input.

11. The method of claim 1 wherein the data source further includes at least one of image acquisition system information and demographic information, symptoms, and history of patient, wherein the image acquisition system information, demographic information, symptoms, and history of patient serve as feature measures in the feature extraction algorithm.

12. The method of claim 4 wherein the feature selection algorithm comprises determining a feature measure's ability to separate regions into different classification groups.

13. The method of claim 12 wherein the feature selection algorithm further comprises ranking each feature measure in the set of feature measures based on each feature measure's ability to separate regions into a classification group.

14. The method of claim 12 wherein the feature selection algorithm further comprises reducing quantity of feature measures by eliminating correlated features.

15. The method of claim 13 wherein the feature selection algorithm further comprises selecting highest ranked feature measure and adding additional feature measures in descending order.

16. The method of claim 1 wherein the dual or multiple energy image set is a dual energy image set comprising a high energy image, a low energy image, a bone image, and a soft tissue image, the method comprising defining regions of interest and incorporating features from all regions of interest on all images.

17. The method of claim 1 wherein the dual or multiple energy image set is a dual energy image set comprising a high energy image, a low energy image, a bone image, and a soft tissue image, the method comprising defining at least one region of interest, employing a feature extraction algorithm, and classifying a candidate region of interest on each image and subsequently combining results of all operations.

18. The method of claim 1 further comprising indicating at least one classified region using a marker on a display of each image within the dual or multiple energy image set where the at least one classified region is located.

19. The method of claim 18 further comprising displaying a single image which incorporates all markers from each image within the dual or multiple energy image set.

20. A system for computer aided processing of dual energy images, the system comprising:

a detector generating a first image representative of photons at a first energy level passing through a structure and a second image representative of photons at a second energy level passing through the structure;

a memory coupled to the detector, the memory storing the first image and the second image;

a processing circuit coupled to the memory, the processing circuit:

processing as inputs features from all images of a dual energy image set including four distinct images that are utilized together, the four distinct images comprising a bone image, a soft tissue image, a high energy image, and a low energy image from the first image and the second image, the features comprising computed features, measured features, or both;

storing the dual energy image set in the memory as a data source, each member of the image set being useable for feature detection computer aided processing together with each other member of the image set, each member of the image set being arranged at the data source in such a manner as to allow the computer aided processing to be performed once by incorporating features from all images of the image set;

defining a region of interest within an image from the dual energy image set;

combining information from all of the four images; and extracting a set of feature measures from the region of interest; and a reporting device coupled to the processing circuit, the reporting device reporting at least one feature.

21. A system for computer aided processing of dual energy images, the system comprising:

detection means for generating a first image representative of photons at a first energy level passing through a structure and a second image representative of photons at a second energy level passing through the structure;

storage means for storing the first image and the second image;

processing means for:

processing as inputs features from all images of a dual energy image set including four distinct images that are utilized together, the four distinct images comprising a bone image, a soft tissue image, a high energy image, and a low energy image from the first image and the second image, the features comprising computed features, measured features, or both;

storing the dual energy image set in the memory as a data source, each member of the image set being useable for feature detection computer aided processing together with each other member of the image set, each member of the image set being arranged at the data source in such a manner as to allow the computer aided processing to be performed once by incorporating features from all images of the image set;

defining a region of interest within an image from the dual energy image set;

combining information from all of the four images;

extracting a set of feature measures from the region of interest;

employing a feature selection algorithm on the set of feature measures and identifying an optimal set of features;

classifying the optimal set of features; and, incorporating prior knowledge from training into classifying the optimal set of features; and display means for displaying at least one classified region of interest.

22. A storage medium encoded with a machine readable computer program code, said code including instructions for causing a computer to implement a method for aiding in processing of dual or multiple energy images, the method comprising:

employing a data source, the data source including a dual or multiple energy image set, the image set comprising four distinct images comprising a high energy image, a low energy image, a bone image, and a soft tissue image, each member of the image set being useable for feature detection computer aided processing together with each other member of the image set, each member of the image set being arranged at the data source in such a manner as to allow the computer aided processing to be performed once by incorporating features from all images of the image set;

processing the image set by utilizing all of the four distinct images together according to the following:

receiving as inputs features from all four of the images of the image set, the features comprising computed features, measured features, or both;

defining a region of interest within an image from the dual or multiple energy image set;

combining information from all of the four images;

extracting a set of feature measures from the region of interest; and, employing a feature extraction algorithm on the feature measures for identifying an optimal set of features.

23. A method for detecting bone fractures, calcifications and metastases, the method comprising:

employing a data source, the data source including a dual or multiple energy image set, the image set comprising four distinct images comprising a high energy image, a low energy image, a bone image, and a soft tissue image, each member of the image set being useable for feature detection computer aided processing together with each other member of the image set, each member of the image set being arranged at the data source in such a manner as to allow processing of the image set to be performed once by incorporating features from all images of the image set;

processing the image set by utilizing all of the four distinct images together according to the following:

receiving as inputs features from all of the four images of the image set, the features comprising computed features, measured features, or both;

utilizing a bone image from the dual or multiple energy image set;

selecting a region of interest within the bone image to search for a calcification, fracture or metastatic bone lesion;

combining information from all of the four images;

segmenting bone from a background of the bone image; and, identifying a candidate region within the bone as a candidate for a calcification, fracture or metastatic bone lesion.

24. The method of claim 23 further comprising classifying an identified candidate region.

25. The method of claim 23 wherein segmenting bone comprises utilizing a region growing algorithm.

26. The method of claim 25 wherein the region growing algorithm is manually initialized by having a user select a seed point.

27. The method of claim 25 wherein the region growing algorithm is automatically initialized by utilizing bone attributes to select a seed point.

28. The method of claim 23 wherein segmenting bone comprises multi-level intensity thresholding.

29. The method of claim 23 wherein identifying a candidate region comprises utilizing an edge detection algorithm.

30. The method of claim 29 wherein image processing using morphological erosion is used for eliminating noise and false edges.

31. The method of claim 29 wherein rib edges are eliminated using a connectivity algorithm.

32. The method of claim 23 wherein classifying identified candidate regions comprises using a computer aided rule based approach, wherein different rules apply for calcifications, metastases and fractures, and for different types of fractures and different properties of metastases.

33. The method of claim 32 wherein rules are based on size measurements of line edges of the identified candidate regions.

34. The method of claim 23 further comprising indicating candidate regions on a display.

35. The method of claim 34 wherein indicating candidate regions comprises placing a marker on the bone image indicative of a classification of the candidate region.

36. A method for detecting lung disease, the method comprising:

employing a data source, the data source including a dual or multiple energy image set, the image set comprising four distinct images comprising a high energy image, a low energy image, a bone image, and a soft tissue image, each member of the image set being useable for feature detection computer aided processing together with each other member of the image set, each member of the image set being arranged at the data source in such a manner as to allow processing of the image set to be performed once by incorporating features from all images of the image set;

processing the image set by utilizing all of the four distinct images together according to the following:

receiving as inputs features from all of the four images of the image set, the features comprising computed features, measured features, or both;
utilizing a soft-tissue image from the dual or multiple energy image set;
selecting a region of interest within the soft-tissue image to search for an indication of disease;
combining information from all of the four images;
segmenting the region of interest from a background of the soft-tissue image;
employing a feature selection algorithm on feature measures for identifying an optimal set of features;
identifying a candidate region within the bone image which correlates to the region of interest in the soft-tissue image;
extracting features from the candidate region in the bone image; and
classifying the region of interest in the soft-tissue image as a candidate for soft-tissue disease utilizing the features extracted from the bone image.

37. The method of claim 36, wherein identifying a disease in the soft-tissue image comprises identifying a solitary pulmonary nodule or lesion, and wherein the features extracted from the bone-image are indicative of calcification of the nodule, the method further comprising utilizing the bone-image calcification features to classify the region of interest in the soft-tissue image as probably benign.

38. The method of claim 36 wherein classifying comprises using a computer aided rule based approach, wherein different rules apply for different medical conditions, and different rules are used for the soft-tissue and bone-images.

39. The method of claim 36 further comprising displaying a single image which incorporates all markers from each image within the dual or multiple energy image set.

40. The method of claim 39 further comprising displaying a single image which incorporates markers uniquely indicative of results from the soft-tissue image that have been further classified based on results from the bone-image.

* * * * *